United States Patent [19]

Chvapil

[11] 4,369,773
[45] Jan. 25, 1983

[54] CONTRACEPTIVE SPONGE - DIAPHRAGM BILAYER

[76] Inventor: Milos Chvapil, 5655 N. Mina Vista, Tucson, Ariz. 85718

[21] Appl. No.: 204,294

[22] Filed: Nov. 5, 1980

[51] Int. Cl.³ .............................................. A61F 5/46
[52] U.S. Cl. ................................... 128/127; 128/270
[58] Field of Search ...................... 128/127, 270, 285

[56] References Cited

U.S. PATENT DOCUMENTS

| | | | |
|---|---|---|---|
| 2,020,107 | 11/1935 | Cruickshank | 128/127 |
| 2,309,868 | 2/1943 | Robertson | 128/127 |
| 2,580,133 | 12/1951 | Sheen | 128/127 |

FOREIGN PATENT DOCUMENTS 822877  11/1951  Fed. Rep. of Germany ...... 128/127

WO79/00000-14  1/1979  PCT Int'l Appl. .

Primary Examiner—C. Fred Rosenbaum

[57] ABSTRACT

An intravaginal insert, serving as a mechanical and chemical contraceptive barrier is described. The insert consists of a thin circular disc bilayer of a resilient and fluid absorbent sponge, preferably made of collagen, laminated on the inside with a soft membrane. Both layers of laminated sponge are connected at the circumference to form a pocket with a small opening. A spermicide, preferably a detergent, is deposited within the matrix of the sponge, which is also buffered to pH 4 to 5. Into a pocket made from this composite material a silastic ring is inserted before wetting the sponge with tap water and inserting it into the upper vault of the vagina to cover the cervix in a similar manner to the standard diaphragm.

2 Claims, 3 Drawing Figures

CONTRACEPTIVE SPONGE - DIAPHRAGM BILAYER

BACKGROUND OF THE INVENTION

Various contraceptive techniques are evaluated as to their conception preventing effectiveness, safety and convenience to the user. The use of the diaphragm is considered one of the safer methods, although the effectiveness, and mainly convenience, is rather poor. In order to be effective, the diaphragm must be used in combination with spermicidal creams, foams, jellies. About one teaspoon of a spermicide should be applied inside the dome, on the convex side of the latex as well as around the circumference of the ring reinforcing the diaphragm structure and enabling its retention and proper intravaginal position. Due to the application of the spermicidal moieties the use of the diaphragm is considered as "messy" by the user as well as her partner. Insufficient amount of spermicidal cream placed on the circumference is probably the main reason, next to improper placement, for contraceptive failure of this method. Still another reason for inconvenience in using the spermicide with rubber diaphragm is the need to administer the jelly, or cream, on the diaphragm no longer than two hours before intercourse. Another inconvenience lies with the need for repetitive application of the spermicide between intercourses. Because the diaphragm is formed of the rubber membrane, it does not absorb liquified ejaculate, which causes the discomfort by dripping.

It is the object of this invention to present a new contraceptive method which eliminates all the above mentioned inconveniences of the diaphragm and in addition offers higher contraceptive effectiveness than the conventional diaphragm contraceptive method.

DESCRIPTION OF THE INVENTION

A thin layer of a sponge-like matrix, characterized by high resiliency, by large fluid binding capacity and by fast wetting is laminated by a thin membrane made of biocompatible plastics. I found that sponges made from collagen by known processes, such as described in U.S. Pat. No. 3,823,212 ,nd U.S. Pat. No. 4,193,813, are very suitable because of large wet resilience and fluid binding properties. In addition, collagen sponge was found safe when administered intravaginally. I also found that collagen sponge matrix will retain solutions of any medications, which when applied intravaginally are slowly released into the vaginal canal. Another material which showed to function adequately was a sponge made of polyvinylalcohol, polyurethane, acetylcellulose and other biologically inert polymers.

The function of the sponge is to serve as reservoir for an efficient spermicide. Another function of fluid absorbent sponge is to retain the liquified ejaculate. Finally, the sponge conthowever, that the sponge layer laminated with a fluid permeable membrane made of unwoven plastic fleece retained and inactivated all the sperm. Thus the impermeability to fluid of the laminating membrane is not an absolute requirement. The main function of the lamination is to reinforce the otherwise fragile thin sponge layer. It makes it also feasible to attach both layers of the sponge together at the circumference of the circular disc.

The attachment of the plastic membrane to one surface of about 0.15 to 0.3 cm thick sponge is achieved, for instance, by insertion between these two structures of a thin layer of double sticking adhesive tape. Two circular discs of a sponge are connected together with the lamination inside at the periphery of the disc. The edges of the membrane are either sealed together by applying a dry heat of 80°–90° C. for 10 to 20 seconds to the 0.3 cm wide outer circumference of the sponges, leaving about 60° of the circumference unattached, forming the shape of a horseshoe. The heat melts only the plastic membranes and forms a pocket with a small opening about 3 to 4 cm wide. I found that sewing the sponges together 0.3 mm from the edge of the disc is also quite satisfactory. Various sizes of the circular pocket will be available to accommodate the silastic rings ranging from 50 to 110 mm diameter, as are offered by commercially available diaphragms to users with varying sizes of their vaginal anatomy.

The sponge bilayer pocket is now immersed into any solution with an effective spermicide, such as detergents, heavy metals, acids. I found that a combination of spermicidal detergent, such as Nonoxynol-9 (p-Nonylpheloxypolyethoxyethanol) and buffered acidity formed by 0.1 M citrate buffer of pH 4.5 is quite effective to inactivate human spermatozoa within less than one minute. The concentration of the solution of the spermicidal detergent is such that it should form 50 to 100 mg deposit of the Nonoxynol-9 within the sponge matrix after the solution evaporates. If the sponge is made of collagen I found it advantageous to add to the solution of detergent in the buffer of pH 4.5 5 to 20 volume percent of glycerin which results in keeping the sponge soft and resilient even when dry.

Before use, the laminated sponge bilayer is wetted by tap water, excess of water is mechanically removed and appropriate size of the commercially available silastic ring is inserted into the pocket. The device is now inserted into the vagina by similar techniques known for commercial diaphragms.

The use of a sponge bilayer containing a spermicide is an aqueous milieu eliminates the messiness of spermicidal creams, foams, jellies. The presence of sponge layer with spermicide at the periphery of the ring coming in contact with the vaginal mucosa forms a tight mechanical and chemical seal against bypassing of sperm. It eliminates also the human error created by the application of insufficient volume of inadequate placement of the cream or similar moieties around the diaphragm.

The use of a fluid absorbent sponge makes it possible that the liquified ejaculate is soaked into the matrix of the sponge. It was determined that due to the presence of the spermicide and acidity (pH 4.5) the spermatozoa are inactivated within 60 seconds contact with the sponge.

The sponge bilayer forms a reservoir for the spermicide, which is slowly and continuously released into the vagina for several days. For this reason, the same contraceptive sponge-diaphragm bilayer could be used during repetitive intercourses.

Another advantage of this contraceptive method consists in the possibility to retrieve in the sponge matrix, remaining spermicidal agent, detergent, at the time of removing the sponge from the vagina. It has been shown that spermicides inserted in the vagina are transported across the vaginal wall to the systemic circulation.

Various construction principles and advantages of this contraceptive method are apparent from the following description and from the accompanying drawings in which FIG. 1 is a diagrammatic top view showing sponge bilayers (1), sewed together (2) and lined with a plastic membrane inside the pocket (5), into which a silastic ring (3) is inserted through an opening (4).

Figure 1:
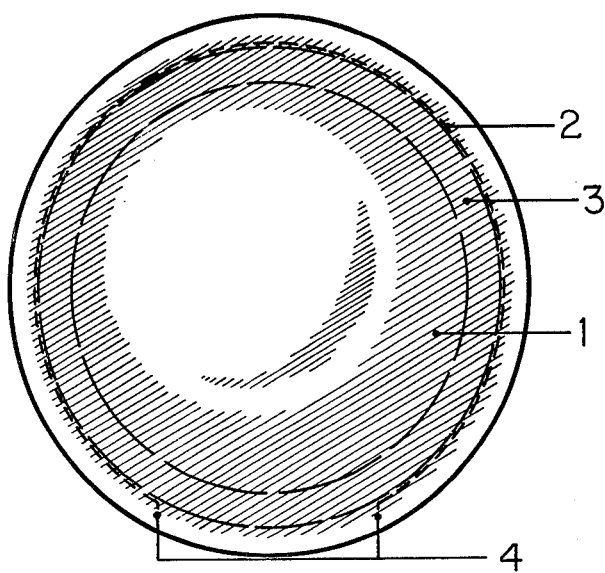
Figure 2:
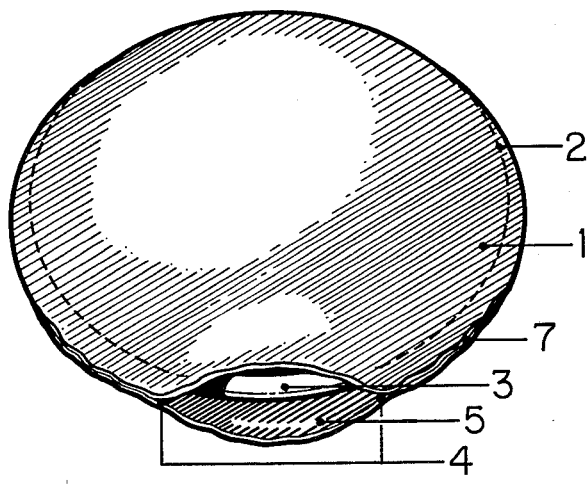
FIG. 2 is a side sectional view illustrating the silastic ring (3) distending the sponge bilayer laminated with plastic membrane. At the circumference of the sponge bilayer loose ends (7) are shown.
Figure 3:
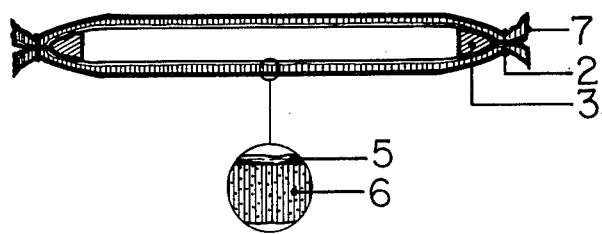
FIG. 3 is a transverse section through the insert. The enlarged section shows the presence of a spermicide (6) within the sponge matrix.

Referring to FIGS. 1-3 of the drawing, the product comprises a sponge laminated on one side with an impermeable thin plastic membrane attached to the sponge by an adhesive. The matrix of the sponge contains spermicidal drugs. Thseveral patents as well as scientific publications. Thus U.S. Pat. No. 4,193,813 claims to use pure collagen sponge cylinder 6 cm wide by 2.5 cm thick with attached fabric loop for easy removal. Because of the bulkiness of this structure, both the insertion and removal of even this size sponge are complicated, requiring special insertor. Larger size sponges of 8 to 10 cm diameter, which would be required for effective contraception by many women of older age and with several vaginal deliveries, are impossible to insert. The sponge not being reinforced by lamination becomes fragile and deteriorates after a few uses. U.S. Pat. No. 3,216,422 improves the commercial diaphragm by inserting in the dome an absorbable material. This invention does not solve the basic problem of the poor seal between the resilient elastic rim and the vaginal wall, which is the major reason for rather low effectiveness of the method. U.S. Pat. No. 3,128,767 by J. J. Nolan deals with hygienic vaginal tampon rather than with contraceptive device. It laminates vaginal tampon at one side with an impermeable membrane fitted with the rim at the circumference in order to retain menstrual flow without the problem of dripping. U.S. Pat. by D. B. Dubin (U.S. Pat. No. 3,786,807) uses absorbable material laminated with a cup of thin synthetic rubber, containing metallic magnetic disc for easy insertion and removal. This, as well as the above patents, does not take advantage of forming a soft seal at the periphery of the insert and the vaginal wall. In addition, my invention stresses the combination of both mechanical and chemical tight fit and contraceptive effect. The patent by H. A. Sheen (U.S. Pat. No. 2,580,133) uses another type of pessary-diaphragm, where, to the surface of a sponge an elastic impermeable sheet is bonded at the vaginal side of the sponge to prevent fluid from passing through. This device is not meant for contraception but rather due to the stiffness of the framework as a surgical prolapsing tissue supporting pessary. Thus, none of the above cited patents uses a thin bilayer of sponge-like or felt-like sheet, laminated on the inside with a plastic thin membrane, where the sponge is impregnated with a spermicide incorporated into an acid environment, the sponge bilayer forming a pocket into which a silastic ring is inserted for reinforcement of the circular disc shape and its retention in the upper vault of the 13
Chvapil—July 9, 1974
U.S. Pat. No. 4,193,813—Chvapil—Mar. 18, 1980
U.S. Pat. No. 2,580,133—Sheen—Dec. 25, 1951
U.S. Pat. No. 3,786,807—Subin—Jan. 22, 1974
U.S. Pat. No. 3,128,767—Nolan—Apr. 14, 1964
U.S. Pat. No. 3,216,422—Steiger et al.—Nov. 9, 1965
U.S. Pat. No. 3,128,767—Nolan—Apr. 14, 1964
U.S. Pat. No. 3,216,422—Steiger et al.—Nov. 9, 1965

What is claimed is:

1. Formation of a contraceptive sponge bilayer product consisting of:
    (a) two layers of sponges having the shape of a circular disc, the diameter of about 5 to 11 cm and of the thickness of about 0.15 to 0.3 cm
    (b) the said sponges, laminated on one side with a thin plastic membrane attached to the sponge surface by an adhesive
    (c) connecting the two laminated sponges together at the circumference of the discs to form a pocket having the plastic membrane inside, the sponge layer outside and leaving an opening into the pocket about 3 to 4 cm wide
    (d) incorporating into the sponge an effective spermicide dissolved in a buffered solution of pH 3 to 5
    (e) the said solution containing 5 to 20 volume percent glycerin or similar plasticizers and
    (f) inserting into the pocket of the laminated sponge bilayer a silastic ring 2. As under claim 1, where the sponge layer is formed by any polymers such as collagen, polyvinylalcohol, polyurethane, acetylcellulose and the like, forming a three dimensional matrix characterized by high resilience, large fluid absorbency and fast wetting.

* * * * *